US009733157B2

(12) United States Patent
Matsumoto et al.

(10) Patent No.: US 9,733,157 B2
(45) Date of Patent: Aug. 15, 2017

(54) AUTOMATIC BLOOD-SAMPLING TUBE PREPARATION SYSTEM

(75) Inventors: Toshikazu Matsumoto, Yokohama (JP); Yoshimi Hirasawa, Yokohama (JP); Yasushi Nakano, Yokohama (JP); Yusuke Wada, Kawasaki (JP); Ichiro Nakamura, Kawasaki (JP)

(73) Assignee: TECHNO MEDICA CO., LTD., Yokohama-shi (JP)

( * ) Notice: Subject to any disclaimer, the term of this patent is extended or adjusted under 35 U.S.C. 154(b) by 146 days.

(21) Appl. No.: 14/117,653

(22) PCT Filed: May 18, 2011

(86) PCT No.: PCT/JP2011/061379
§ 371 (c)(1),
(2), (4) Date: Jan. 17, 2014

(87) PCT Pub. No.: WO2012/157086
PCT Pub. Date: Nov. 22, 2012

(65) Prior Publication Data
US 2014/0133941 A1 May 15, 2014

(51) Int. Cl.
*G01N 1/10* (2006.01)
*A61B 5/153* (2006.01)
(Continued)

(52) U.S. Cl.
CPC ............... *G01N 1/10* (2013.01); *A61B 5/153* (2013.01); *A61B 5/150274* (2013.01);
(Continued)

(58) Field of Classification Search
CPC ............. A61B 5/1405; A61B 5/150274; A61B 5/150795; A61B 5/150786; B01L 3/5453;
(Continued)

(56) References Cited

U.S. PATENT DOCUMENTS

2003/0207456 A1* 11/2003 Ostgaard ............ B01L 3/50825
436/43
2005/0159982 A1* 7/2005 Showalter ............ G06F 19/366
705/2
(Continued)

FOREIGN PATENT DOCUMENTS

JP          2834595 B2    12/1998
JP       2004-347376 A    12/2004
(Continued)

OTHER PUBLICATIONS

International Search Report (in Japanese with English translation) for PCT/JP2011/061379, mailed Aug. 30, 2011; ISA/JP.

*Primary Examiner* — Jill Warden
*Assistant Examiner* — Benjamin Whatley
(74) *Attorney, Agent, or Firm* — Harness, Dickey & Pierce, P.L.C.

(57) ABSTRACT

The present invention provides an automatic blood-sampling tube preparation system which can reduce the reading mistake of the information of the RFID tags by selectively taking out a blood-sampling tube required to an examination of a patient according to a doctor's instruction information from the blood-sampling tube containing section, writing the patient examination information on a RFID tag of the taken out tube on the basis of the instruction information, reading simultaneously all patient examination information from all RFID tags contained in the prepared container for every patient, and comparing the information read from the RFID tags with the instruction information to ensure accuracy.

8 Claims, 7 Drawing Sheets (51) Int. Cl.
*G06Q 50/24* (2012.01)
*G01N 35/00* (2006.01)
*B01L 3/00* (2006.01)
*A61B 5/15* (2006.01)
*A61B 5/154* (2006.01)
*B65C 9/00* (2006.01)

(52) U.S. Cl.
CPC ...... *A61B 5/150793* (2013.01); *B01L 3/5453* (2013.01); *G01N 35/00732* (2013.01); *G06Q 50/24* (2013.01); *A61B 5/15003* (2013.01); *A61B 5/154* (2013.01); *A61B 5/150259* (2013.01); *B01L 2300/021* (2013.01); *B01L 2300/022* (2013.01); *B65C 2009/0003* (2013.01); *G01N 2035/00782* (2013.01); *G01N 2035/00801* (2013.01); *G01N 2035/00831* (2013.01)

(58) Field of Classification Search
CPC ......... B01L 2300/021; B01L 2300/022; G01N 35/00732; G01N 2035/00742; G01N 2035/00782; G01N 2035/00801; G01N 2035/00831; B65C 2009/0003
See application file for complete search history.

(56) References Cited

U.S. PATENT DOCUMENTS

| | | | | |
|---|---|---|---|---|
| 2007/0013541 | A1* | 1/2007 | Harazin | G01N 35/00732 340/8.1 |
| 2010/0018330 | A1* | 1/2010 | Marty | G01N 35/00732 73/864.81 |
| 2010/0159603 | A1* | 6/2010 | Hamada | G01N 35/00 436/47 |

FOREIGN PATENT DOCUMENTS

| | | | | |
|---|---|---|---|---|
| JP | 2004347376 A | * | 12/2004 | ............... B65C 3/02 |
| JP | 2005-121558 A | | 5/2005 | |
| JP | 2005121558 A | * | 5/2005 | ............... G01N 1/10 |
| JP | 2008-220995 A | | 9/2008 | |
| JP | 2009077795 A | * | 4/2009 | ............... A61B 5/15 |

* cited by examiner

AUTOMATIC BLOOD-SAMPLING TUBE PREPARATION SYSTEM

TECHNICAL FIELD

The present invention relates to the improvement of an automatic blood-sampling tube automatic preparation system.

BACKGROUND OF THE INVENTION

If the blood-sampling tube with the collected blood has no information for specifying a patient, it is impossible to identify the patient from when the blood is collected. Therefore the name of the patient whose blood is to be collected previously is written on a surface of the blood-sampling tube before collecting blood to identify the blood-sampling tube after blood collecting.

Recently, in most cases, vacuum blood-sampling tubes are used for collecting blood. Since reaction medicine or a treating solution are previously stored in the vacuum blood-sampling tubes, the use of the vacuum blood-sampling tubes are previously decided in accordance with an examination that should be carried out. Therefore, when collecting blood from a patient, one or more vacuum blood-sampling tubes which can be used for the examination of the patient must be previously selected.

For this reason, the hospital staff, such as a nurse, selects and takes out beforehand one or more vacuum blood-sampling tubes required to the examination of the patient from many kinds of blood-sampling tubes, before collecting blood. And the hospital staff writes the name of the patient whose blood is to be collected on the surface of the taken-out blood-sampling tubes. The above-mentioned works are dramatically complicated and must be done very carefully which tends to make the hospital staff tired.

In order to solve above problem, the automatic blood-sampling tube preparation system, which can automate preparation of one or more blood-sampling tubes required to the examination of the patient, has already proposed (Japanese Patent No. 2834595B).

The automatic blood-sampling tube preparation system stores the blood-sampling tubes of a plurality of kinds in separate blood-sampling tube containing cases for each kind. The preparation device automatically selects a blood-sampling tube required to the examination for the patient, takes out the selected blood-sampling tube from the corresponding blood-sampling tube containing case, prints patient information on a label to make an identification label, automatically pastes the identification label on an outer surface of the taken-out blood-sampling tube, and then collects one or more blood-sampling tubes, each having the identification label, for each patient into a tray or a bag.

The automatic blood-sampling tube preparation system may automatically prepare for each patient the blood-sampling tubes required to the examination of the patient, each blood-sampling tube having the label with the name of patient printed. Therefore, it becomes unnecessary for the hospital staff to make preparations of the blood-sampling tubes before blood collecting.

However, in the construction of the above-mentioned conventional automatic blood-sampling tube preparation system, it cannot be checked whether the prepared blood-sampling tubes i.e. the blood-sampling tubes contained in the tray for each patient are correct on the basis of the instructions of the doctor.

Basically, if the automatic blood-sampling tube preparation system is functioning normally, an exact number of required blood-sampling tubes should be stored in the tray. However, for example, when putting the label pasted blood-sampling tube into the tray, the blood-sampling tube may bound on the tray and may fall from the tray. Also while storing the prepared blood-sampling tubes in a tray, or while carrying a tray in which the blood-sampling tubes are contained to a blood collecting stand, a blood-sampling tube may fall from the tray.

There is a low probably that the above accidents will happen. However, taking into consideration that a serious disease may be discovered in the stage of an examination, blood collecting mistakes owing to the mistake of the preparatory step of a blood-sampling tube must be avoided.

In order to solve the above-mentioned problem, an automatic blood-sampling preparation system is proposed, the system may being constituted to paste the RFID tag label in which information for identifying a patient is written on the blood-sampling tube, read simultaneously the information of all the RFID tags of the labels pasted on the blood-sampling tubes contained in the tray and check whether the blood-sampling tubes are correct in the tray (Japanese Kokai No. JP2004-347376A).

DESCRIPTION OF THE INVENTION

Problem(s) to be Solved by the Invention

According to the above mentioned automatic blood-sampling tube preparation system, it simultaneously read the information from the all RFID tags pasted on the blood-sampling tubes which are contained in the tray and judge whether the kinds of the blood-sampling tubes contained in the tray are correct and/or whether the number of blood-sampling tubes contained in the tray is correct. Therefore, it becomes possible to reduce the mistake of the preparation step of the blood-sampling tubes.

However, the blood-sampling tubes stored in the tray are not necessarily located in the same direction with regularity. Depending on the state/orientation of the blood-sampling tubes stored in the tray, the preparation system may be unable to simultaneously read the information of a part of RFID tags contained in the tray.

When the reading mistake of the information of the RFID tags arises, although it is correct in the number and kinds of blood-sampling tubes stored in the tray, the preparation system may be stopped.

An object of the present invention is to provide an automatic blood-sampling tube preparation system which can solve the above-mentioned conventional problem and reduce the reading mistake of the information of the RFID tags.

Means for Solving the Problem

In order to achieve the above mentioned object, an automatic blood-sampling tube preparation system comprising
at least two blood-sampling tube containing sections each of which is intended to contain blood-sampling tubes of a same type,
a tube transferring means for selectively taking out a blood-sampling tube required to an examination of a patient according to a doctor's instruction information from the related blood-sampling tube containing section and transferring the taken-out blood-sampling tube, a writing means for writing patient examination information on a RFID tag of the blood-sampling tube based on the instruction information, a receiving container transferring means for transferring a prepared container in which the written blood-sampling tubes are contained for each patient, a reading means which is arranged in a transferring path of the container transferring means for reading simultaneously all patient examination information from the all blood-sampling tubes contained in the prepared container while the prepared container transferred by the receiving container transferring means, and a control means for controlling the operations of the said means and comparing the patient examination information read from the RFID tags by the reading means with the instruction information wherein the control means is constituted such that if the control means judges that the patient examination information read from the RFID tags do not match the instruction information, the control means makes the prepared container move so as to change the state/orientation of the RFID tags contained in the prepared container, after that the control means controls the reading means to read the patient examination information from the RFID tags contained the prepared container again, and then the control means compares the patient examination information and the instruction information.

In this specification, "the instruction information from the doctor" includes "the patient examination information". And "the patient examination information" includes at least the sample information such as the sample ID. Also "the patient examination information" may include the patient ID or the examination information.

Also the prepared container contains the hand pasting label and/or the blood-sampling instruction paper in addition to the blood-sampling tubes. In this case, preferably, the hand pasting label is a label with a RFID tag. And the patient examination information may be written on the RFID tag of the label. When the prepared container contains the blood-sampling tubes as well as the hand pasting RFID tag label the reading means read simultaneously the patient examination information from RFID tags of the blood-sampling tube and the hand pasting label, and the control means compares the patient examination information read from the RFID tags of the blood-sampling tubes and hand pasting label with the instruction information from the doctor. And then if the patient examination information read from the RFID tags do not match the instruction information from the doctor, the control means makes the prepared container move so as to change the state/orientation of the blood-sampling tubes and the hand pasting label contained in the prepared container. As a result, the state/orientation of the RFID tags of the blood-sampling tube and the hand pasting label are changed.

Preferably, the prepared container may be moved so as to change the state/orientation of the articles contained therein by controlling the operation of the container transferring means. "The articles contained in the prepared container" may be only the blood-sampling tubes. Also "the articles contained in the prepared container" may include the hand pasting label as well as the blood-sampling tubes. By changing the state/orientation of the articles contained the prepared container, the state/orientation of the RFID tag also are changed.

Also the automatic blood-sampling tube preparation system according to the present invention may further comprise a label pasting means for pasting the RFID tag label on the blood-sampling tube transferred by said tube transferring means. In this case, said writing means may be constituted to write the patient examination information on the RFID tag of the label. Furthermore, preferably, a printing means for printing the patient examination information on a surface of the RFID tag label may be provided on the automatic blood-sampling tube preparation system.

If the RFID tag is previously incorporated in the blood-sampling tube, the writing means may be constituted to write the patient examination information on the RFID tag incorporated in the blood-sampling tube.

Furthermore, the automatic blood-sampling tube preparation system according to the present invention may be constituted such that said container transferring means comprises a lifting means for lifting up and down the container and the control means controls the lifting means such that a part of the prepared container is lifted by the lifting means so as to change the state/orientation of the articles contained in the prepared container.

Also, the automatic blood-sampling tube preparation system according to the present invention may be constituted such that said container transferring means comprises at least one conveyor on which the container is put for transferring the container and the control means controls the conveyor such that the conveyor rapidly starts to move forward, rapidly starts to move rearward and/or rapidly stops so that the state/orientation of the articles contained in the prepared container are changed.

Also for example the automatic blood-sampling tube preparation system according to the present invention may be constituted such that the control means controls both of the operations of the lifting means and the conveyor so as to change the state/orientation of the articles contained in the prepared container.

SUMMARY OF THE INVENTION

An automatic blood-sampling tube preparation system according to the present invention comprises at least two blood-sampling tube containing section each of which is intended to contain blood-sampling tubes of a same type, a tube transferring means for selectively taking out a blood-sampling tube required to an examination of a patient according to an instruction information from a doctor from the blood-sampling tube containing section and transferring the taken-out blood-sampling tube, a writing means for writing patient examination information on a RFID tag of the blood-sampling tube based on the instruction information, a receiving container transferring means for transferring the prepared container in which the written blood-sampling tubes are contained for each patient, a reading means which is arranged in a transferring path of the container transferring means for reading simultaneously all patient examination information from the all blood-sampling tubes contained in the prepared container while the prepared container transferred by the receiving container transferring means, and a control means for controlling the operation of the said means and comparing the patient examination information read from the RFID tags by the reading means with the instruction information wherein the control mean is constituted such that if the control means judges that the patient examination information read from the RFID tags do not match the instruction information, the control means makes the prepared container move so as to change the state/orientation of the RFID tags contained in the prepared container, after that the control means controls the reading means to read the patient examination information from the RFID tags contained the prepared container again, and then the control means compares the patient examination information and the instruction information.

Therefore, owing to the reading error of the reading device, the system does not stop the automatic blood-sampling preparation device or does not sound an error alarm.

Since the automatic blood-sampling tube preparation system according to the present invention changes the state/orientation of the blood-sampling tubes in the prepared container by moving the container using the container transferring means, it does not need to add the mechanism for exclusive use for only changing the states/orientations of the articles in the tray.

Therefore, in order to perform the retry control, a complicated composition is not needed, and the retry control can apply to the existing automatic blood-sampling tube preparation system easily.

BRIEF DESCRIPTION OF THE DRAWINGS

FIGS. 7 (*a*) to (*d*) show a conveyor belt 24 and a first lifting means 25 under a retry control.

DETAILED DESCRIPTION

Referring accompanying drawings, there will be described an embodiment of an automatic blood-sampling tube preparation system according to the present invention hereinafter.

Figure 1:
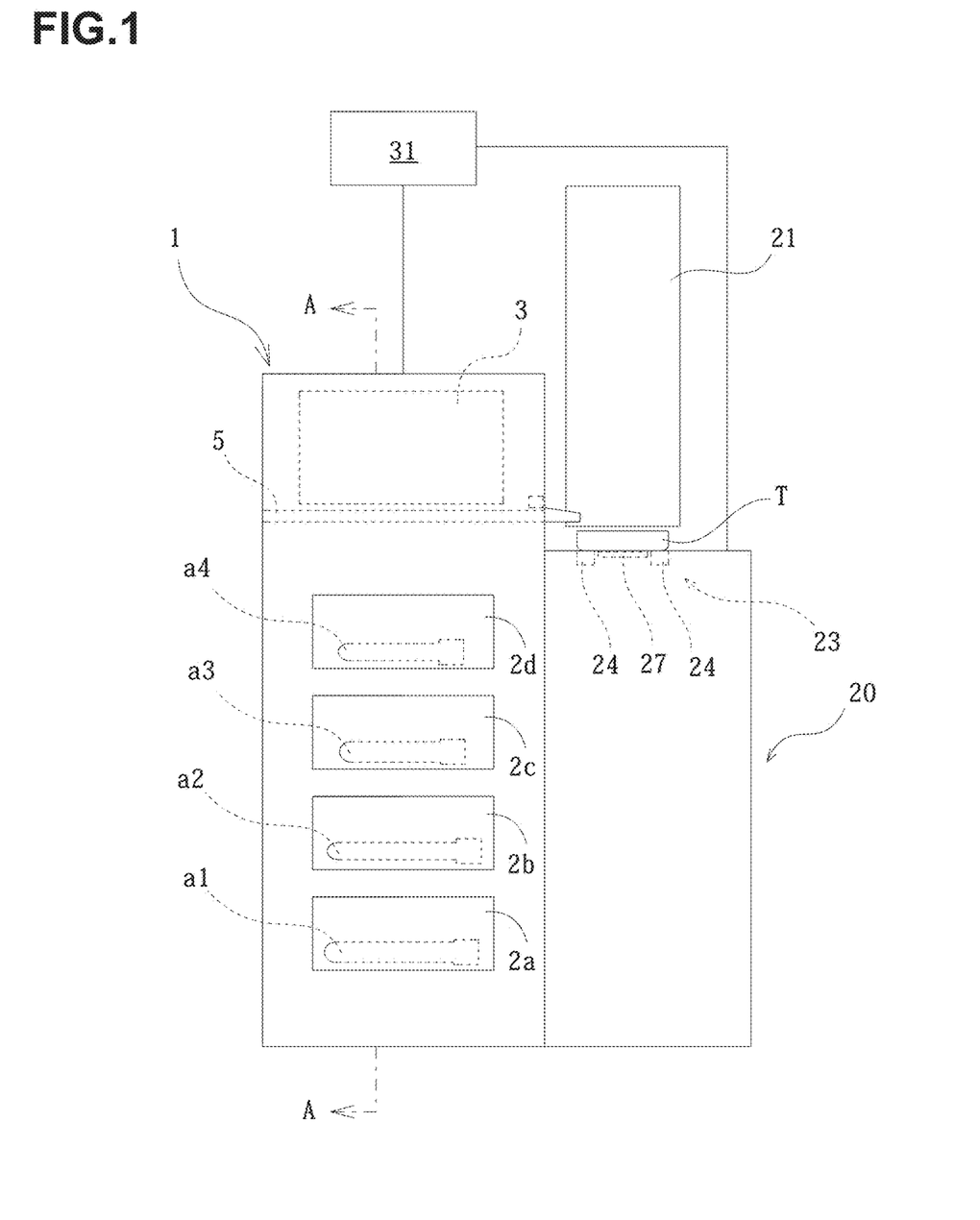
FIG. 1 is a schematic front view showing an embodiment of the automatic blood-sampling tube preparation system according to the present invention.
Figure 2:
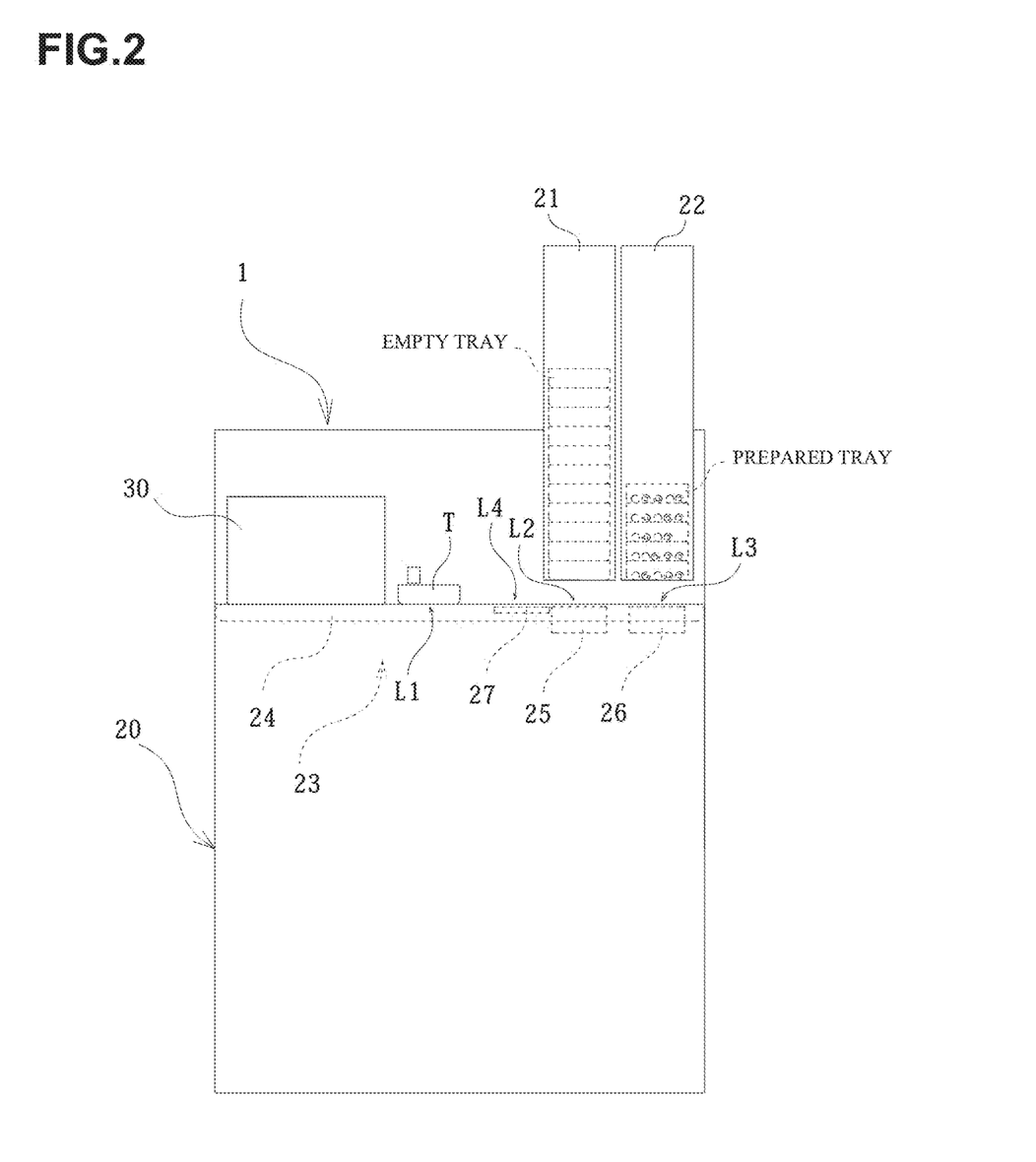
FIG. 2 is a schematic right side view showing the automatic blood-sampling tube preparation system shown in FIG. 1.
Figure 3:
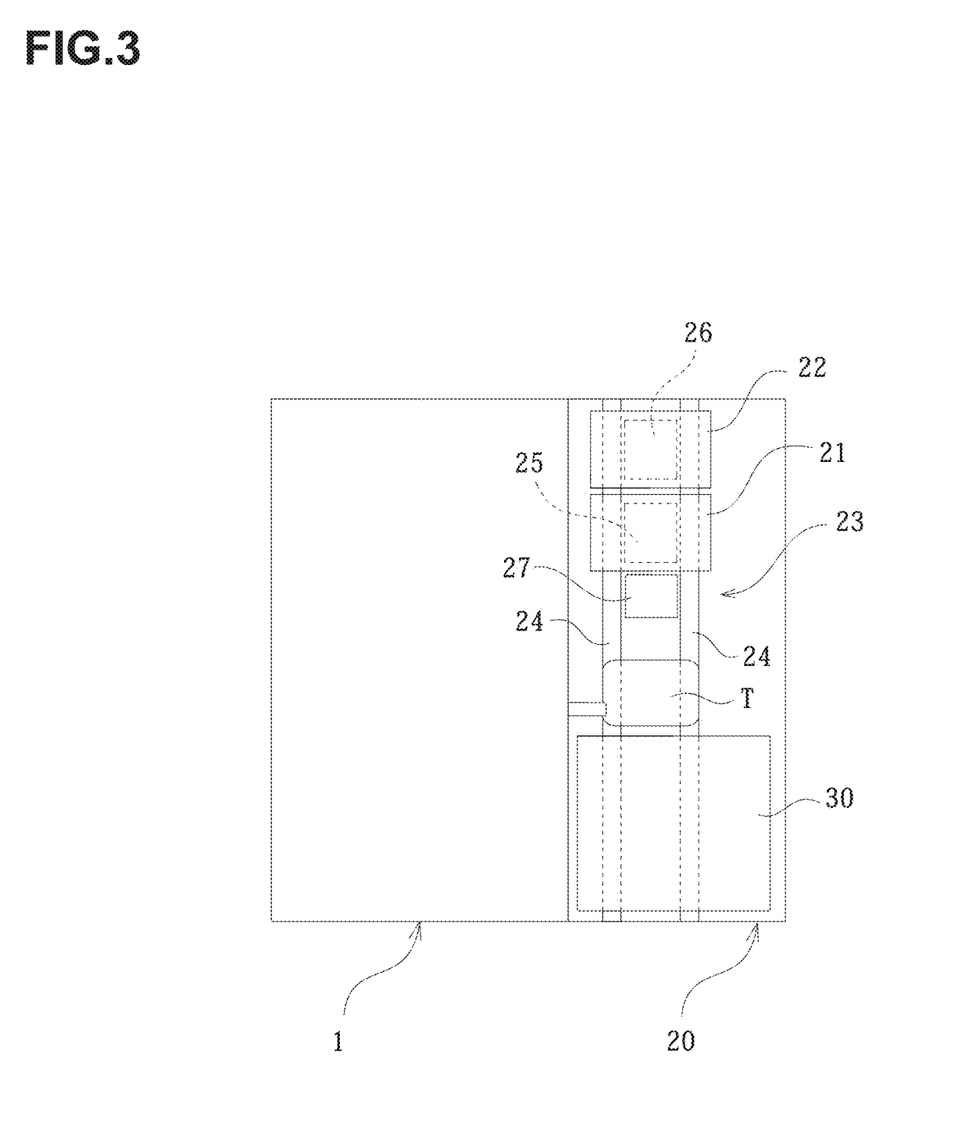
FIG. 3 is a schematic top view showing the automatic blood-sampling tube preparation system shown in FIG. 1.
Figure 4:
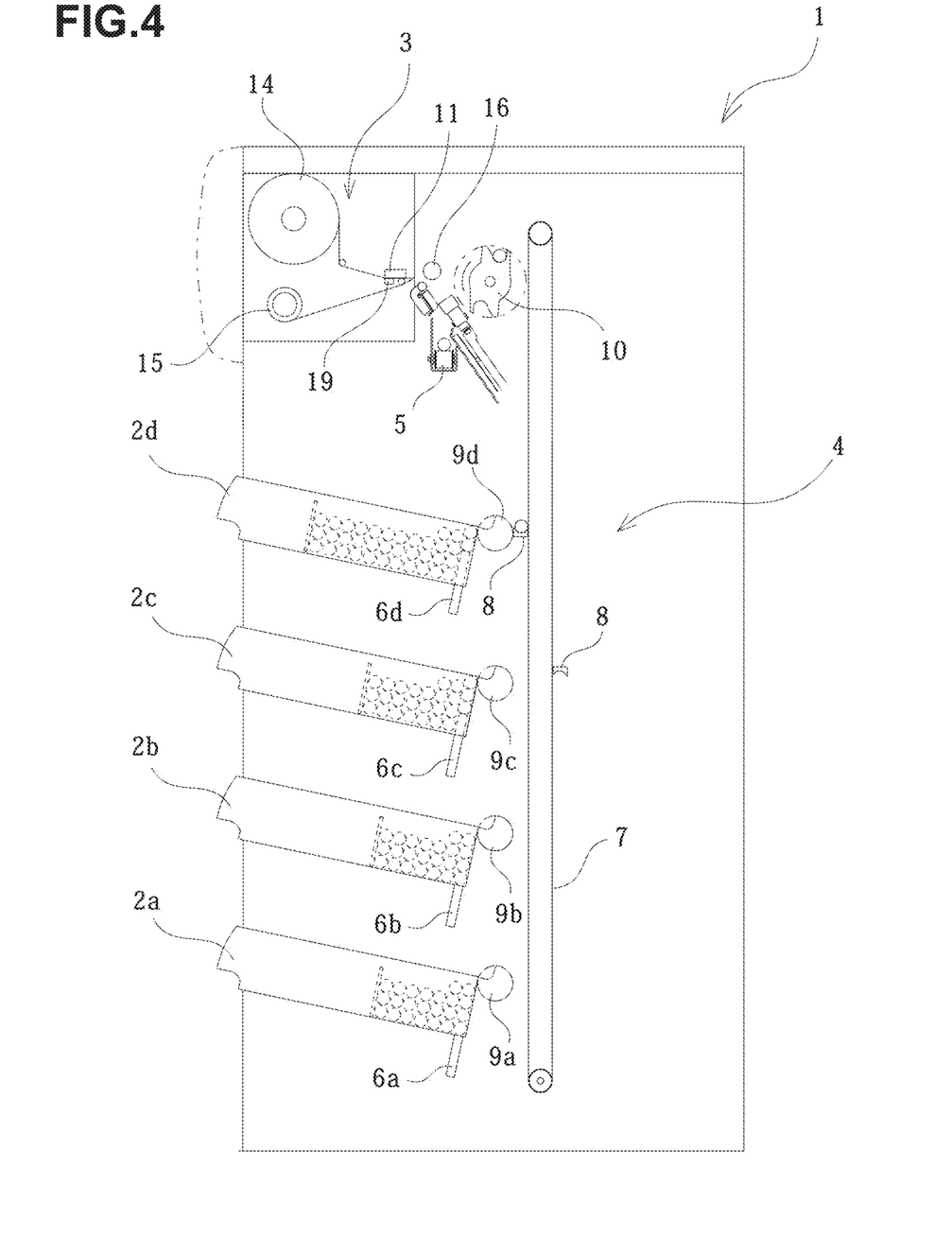
FIG. 4 is a schematic cross sectional view along the A-A line in FIG. 1.

FIG. 1 is a schematic front view showing an embodiment of the automatic blood-sampling tube preparation system according to the present invention. FIG. 2 is a schematic right side view showing the automatic blood-sampling tube preparation system shown in FIG. 1. FIG. 3 is a schematic top view showing the automatic blood-sampling tube preparation system shown in FIG. 1. FIG. 4 is a schematic cross sectional view along the A-A line in FIG. 1.

The automatic blood-sampling tube preparation system comprises an automatic blood-sampling tube preparation device 1 and a blood-sampling tube recovery device 20.

The automatic blood-sampling tube preparation device 1 is provided with four blood-sampling tube containing sections 2*a*-2*d* for containing the bloods-sampling tubes a1-a4 respectively, a tube transferring means 4 (e.g., a tube transferring device 4) for selectively taking out one or more blood-sampling tubes required to one of more examinations from the corresponding blood-sampling tube containing section and transferring the taken-out blood-sampling tubes to a label processing means 3 which prints any information on a label, writes any information on a RFID tag provided on the label, and pastes said label with RFID tag up on the blood-sampling tube, and a discharge conveyer 5 for discharging the label pasted blood-sampling tube. Said tube transferring means 4 comprises four pushing means 6*a*-6*d* for pushing out the blood-sampling tube from each of the blood-sampling tube containing sections 2*a*-2*d*. The tube transferring means 4 also comprises four first delivery means 9*a*-9*d* each of which receives the blood-sampling tube taken out by the each pushing means 6*a*-6*d* and passes the received blood-sampling tube to a rack 8 provided on a transferring conveyor 7. Said transferring conveyor 7 extends to the label processing means 3 arranged in an upper portion of the automatic blood-sampling tube preparation device 1 along the four blood-sampling tube containing sections 2*a*-2*d*. The tube transferring means 4 further comprises a second delivery means 10 which receives the blood-sampling tube from the rack 8 of the transferring conveyor 7 and passes the received blood-sampling tube to a label pasting position X of the label processing means 3.

Figure 5:
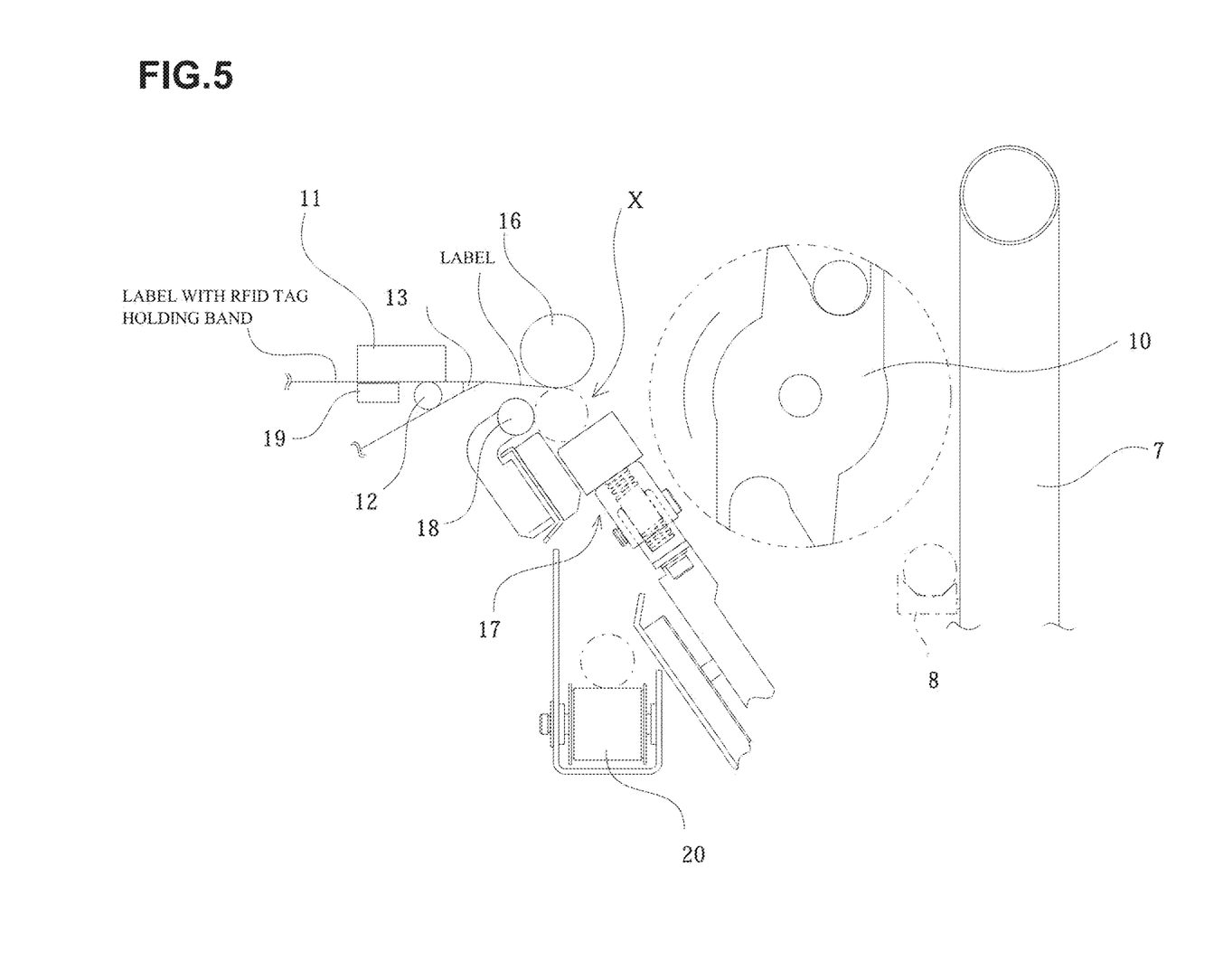
FIG. 5 is an enlarged view of a label processing means 3.

As shown in FIG. 5, the label processing means 3 comprises a printer 11 for printing information with respect to one or more examinations of a patient, i.e. patient examination information, on a label provided with a RFID tag, i.e. a RFID tag label, a platen roller 12, a peeling member 13, a RFID tag label holding band feed roller 14, a label holding band recovery roller 15, a pasting roller 16, a pressing means 17, and a support roller 18. The label processing means 3 also comprises a writing device 19 for writing the patient examination information on the RFID tag of the label. Said pasting roller 16, the support roller 18 and the pressing means 17 are arranged to define the label pasting position X together.

Said label printer 11 prints the patient examination information on the surface of the RFID tag label with the form of a bar code and characters based on the doctor's instruction information about the examination of the patient corresponding to the blood-sampling tube transferred to the label pasting position X.

Also the writing device 19 writes the patient examination information on the RFID tag of the label based on the instruction information of the doctor corresponding to the blood-sampling tube transferred to the label pasting position X.

Here, the patient examination information is information for managing the blood-sampling tube and the sample therein before and after blood collecting, and, specifically, includes sample information including a sample ID and so on. Also, the patient examination information may include a patient ID, a patient name, etc. if needed.

The printed and written RFID tag label is sent towards between the blood-sampling tube positioned in the label pasting position X and said pasting roller 16, so that the label is pasted on the blood-sampling tube by the pasting roller 16, the support roller 18 and the pressing means 17 in the label pasting position X.

Figure 6:
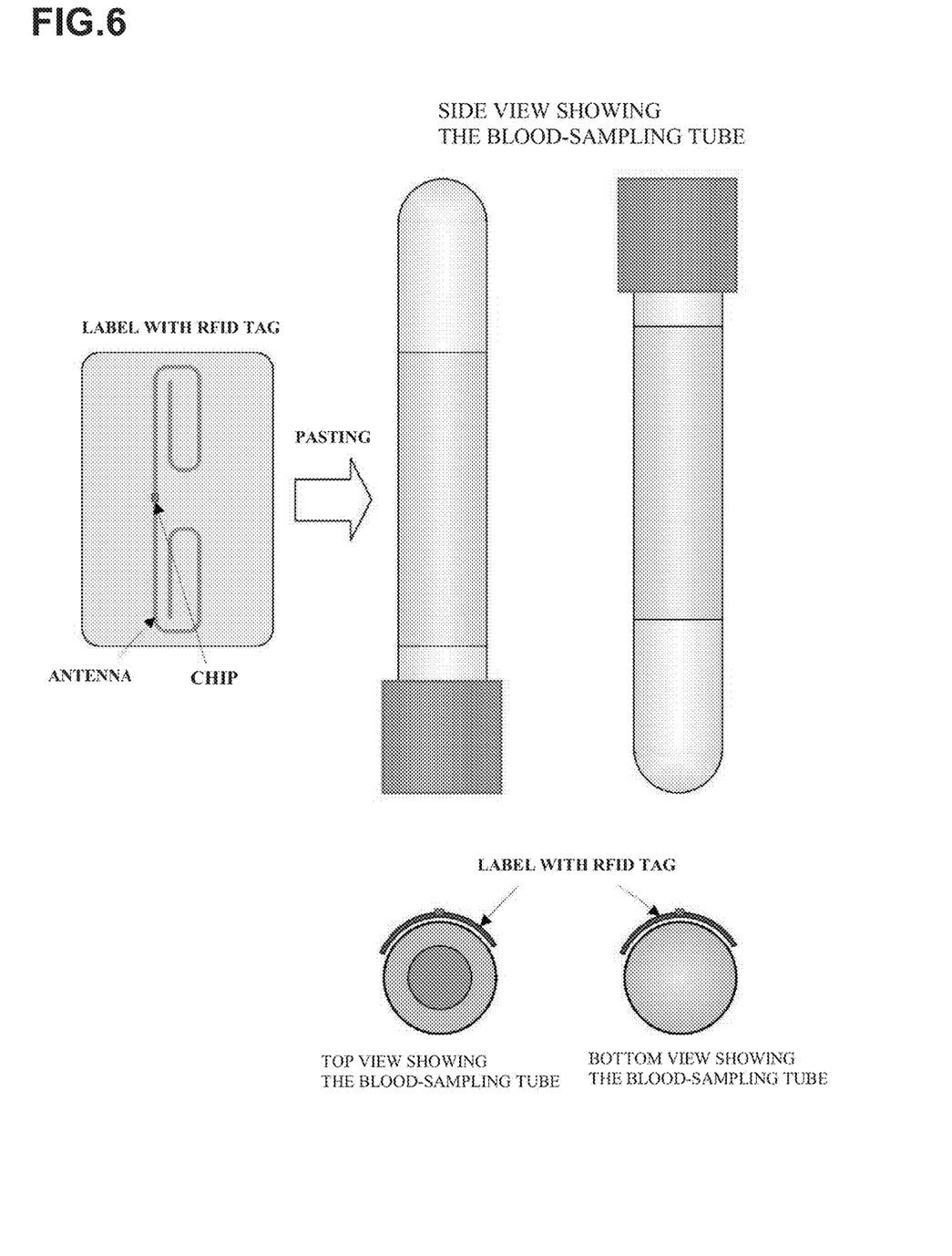
FIG. 6 shows a label with a RFID tag used in the label processing means 3 and a blood-sampling tube on which the label is pasted.

FIG. 6 shows the RFID tag label used in the label processing means 3 and the blood-sampling tube on which the label is pasted. As shown in the FIG. 6, the RFID tag label comprises a printing surface, an antenna and a chip. The antenna and the chip are disposed under the printing surface. The RFID tag label is constituted so that the patient examination information may be printed on the printing surface thereof and may be written in the chip thereof. It is not required that items of the patient examination information printed on the printing surface of the label and items of the patient examination information written in the chip of a RFID tag are completely the same. Specifically, since the information printed on the printing surface of the label is used also for visual confirmation, it is desirable to include the item of the patient name in the printed information. However, since the information written in the chip of the RFID tag is not use for visual confirmation, it is not necessary to include the item of the patient name in the written information.

The label pasted blood-sampling tube is dropped on the discharging conveyor 5 which is disposed under the label processing means 3, and is discharged from the automatic blood-sampling tube preparation device 1 by this conveyor 5.

A blood-sampling tube recovery device 20 is arranged beside the automatic blood-sampling tube preparation device 1. The blood-sampling tube recovery device 20 is constituted so that one or more label pasted blood-sampling tubes which are discharged from the automatic blood-sampling tube preparation device 1 may be stored for every patient in a tray T as a receiving container according to the present invention.

Specifically, the blood-sampling tube recovery device 20 has an empty tray containing section 21 in which one or more empty trays are accumulated and stored.

Also the blood-sampling tube recovery device 20 comprises a prepared tray containing section 22 in which one or more prepared trays which contain one or more label pasted blood-sampling tubes for one patient respectively are accumulated and stored.

Further the blood-sampling tube recovery device 20 comprises a receiving container transferring means 23.

The receiving container transferring means 23 is provided with two conveyor belts 24 which are separated mutually and are arranged in parallel each other.

Said two conveyor belts 24 are arranged so that both belts 24 may pass through a blood-sampling tube receiving position L1, an empty tray receiving position L2, and a prepared tray discharging position L3.

At the blood-sampling tube receiving position L1, the tray laid on the conveyor belts 24 receives the label pasted blood-sampling tube discharged by the discharge conveyor 5 from the automatic blood-sampling tube preparation device 1.

At the empty tray receiving position L2, the conveyor belts 24 receive the empty tray supplied from the empty tray containing section 21.

At the prepared tray discharge position L3, the conveyor belts 24 send the prepared tray to the prepared tray containing section 22.

In this embodiment, the blood-sampling tube receiving position L1, the empty tray receiving position L2 and the prepared tray discharge position L3 are sequentially arranged on a straight line.

A first lifting means 25 (e.g., a first lifting device 25) is arranged at the empty tray receiving position L2 between the two conveyor belts 24. The first lifting means 25 takes out an empty tray from the empty tray containing section 21 and takes it on the conveyor belts 24. A second lifting means 26 (e.g., a second lifting device 26) is arranged at the prepared tray discharge position L3 between two conveyor belts 24. The second lifting means 26 lifts up the prepared tray in which the one or more label pasted blood-sampling tubes are contained from the conveyor belts 24 and pushes it into the prepared tray containing section 22.

Furthermore in this embodiment, a reading device 27 for reading the patient examination information from the RFID tags is arranged in a reading position L4 between two conveyor belts 24. The reading position L4 is positioned between the blood-sampling tube receiving position L1 and the empty tray receiving position L2.

In FIGS. 2 and 3, a numeral number 30 indicates an instruction paper issuing device. The instruction paper issuing device 30 makes a blood-sampling instruction paper based on the instruction information of the doctor and discharges it into the tray positioned in the blood-sampling tube receiving position L1.

Also the instruction paper issuing device 30 makes one or more hand pasting labels for manual pasting if needed based on the instruction information of the doctor. One or more hand pasting labels are issued when one or more blood sampling tubes of the kind which are not contained in the automatic blood sampling tube preparation device are used for the examination of the patient. Said hand pasting labels are also the RFID tag labels. Based on the instruction information of the doctor, the patient examination information is printed on the label and is written on the RFID tag.

Said automatic blood-sampling tube preparation device 1, the blood-sampling tube recovery device 20 and the instruction paper issuing device 30 are controlled by a control device 31.

The control device 31 controls the blood-sampling tube transferring means 4 such that the blood-sampling tube required for the examination of the patient is taken out the corresponding blood-sampling tube containing section 2a-2d and the taken-out blood-sampling tube is transferred to the label processing means 3 on the basis of the instruction information of the doctor. Also the control device 31 controls the label processing means 3 such that the patient examination information corresponding to the transferred blood-sampling tube is printed on the label and is written on the RFID tag of the label and the printed and written label is pasted on the transferred blood-sampling tube. Furthermore the control device 31 controls the discharging conveyor 5 to discharge the label pasted blood-sampling tube from the automatic blood-sampling tube preparation device 1.

Also the control device 31 controls the first lifting means 25 to take out an empty tray from the empty tray containing section 21, and to put it on the conveyor belts 24. The control device 31 also controls the conveyor belts 24 such that the empty tray taken out from the empty tray containing section 21 is transferred to the blood-sampling tube receiving position L1.

The control device 31 controls the conveyor belts 24 to stop the tray at the blood-sampling tube receiving position L1 until the label pasted blood-sampling tubes, the instruction paper and the hand pasting labels if needed which are required to the examination of the one patient are completely contained in the tray.

All of these articles are contained in the tray, and then the control device 31 controls the conveyor belts 24 to transfer the prepared tray to the reading position L4.

When the prepared tray arrives at the reading position L4, the reading device 27 reads simultaneously all of the patient examination information in the RFID tags of the all articles (namely, the blood-sampling tubes and the hand pasting labels if needed) in the prepared tray.

The control device 31 compares the all patient examination information read from the RFID tags with the instruction information of the doctor.

When the patient examination information read from the RFID tags coincide with the patient examination information included in the instruction information of the doctor, the control device 31 controls the conveyor belts 24 to transfer the prepared tray to the prepared tray discharge position L3. And then the control device 31 controls the second lifting means 26 to lift up the prepared tray positioned at the position L3 to the prepared tray containing section 22.

The control device 31 performs a retry control, when the patient examination information read from the RFID tags do not coincide with the patient examination information included in the instruction information of the doctor.

Hereinafter, the retry control will be explained.

FIGS. 7(a) to (d) show the functions of the conveyor belts 24 and the first lifting means 25 during the retry control.

Figure 7:
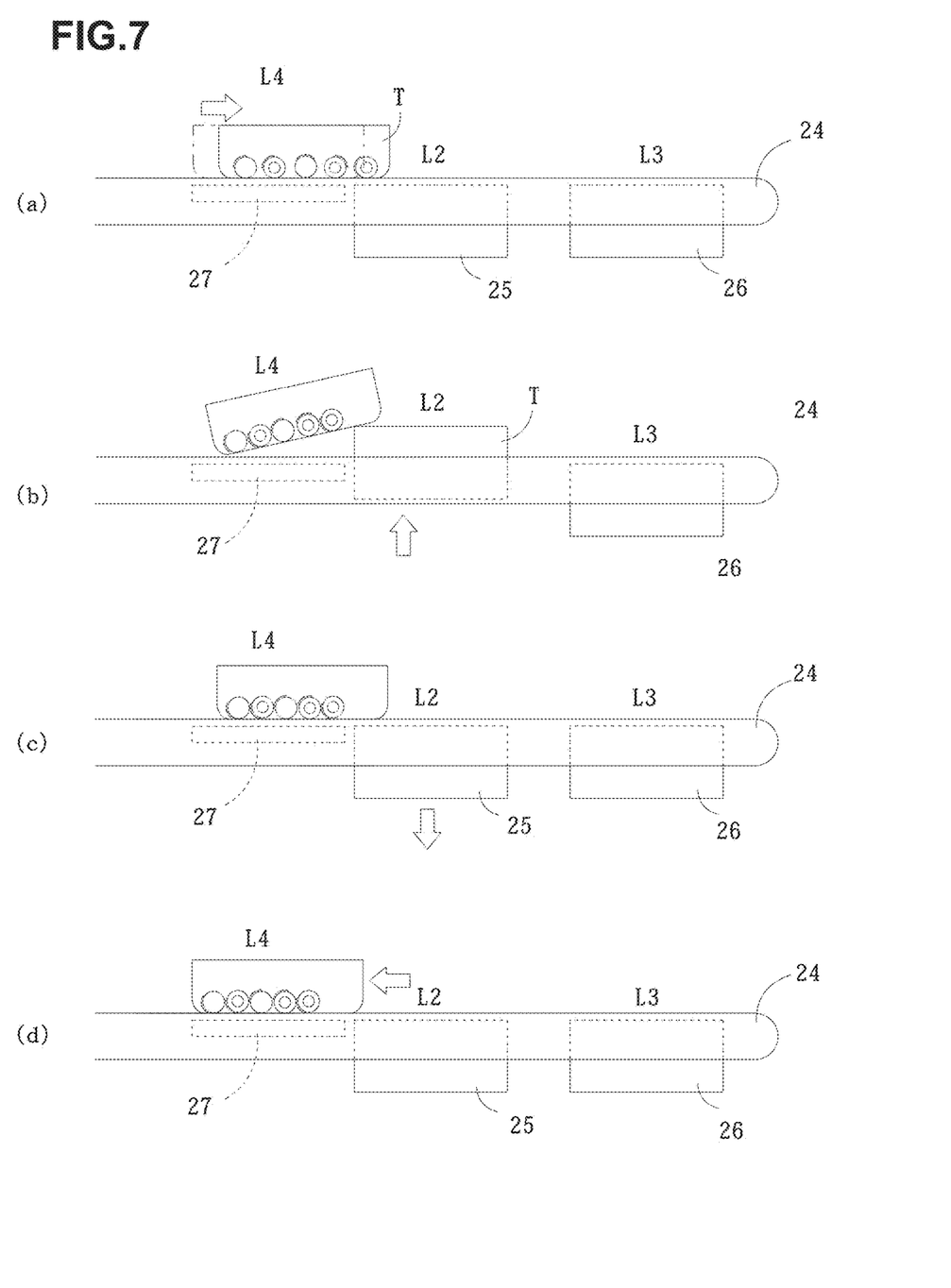

As shown in FIG. 7 (a), in case that the patient examination information read from the RFID tags do not coincide with the instruction information of the doctor, the control device 31 controls the conveyor belts 24 such that the prepared tray is transferred to a position where a part of the prepared tray overlaps above the first lifting means 25.

Subsequently, the control device 31 controls the first lifting means 25 to rise so as to fully incline the prepared tray (FIG. 7 (b)). After that the control device 31 lowers the first lifting means 25 to the lowest position thereof so that the prepared tray puts on the conveyor belts 24 (FIG. 7 (c)).

Then, the control device 31 makes the conveyor belts 24 transfer the prepared tray to the reading position L4 again, and makes the reading device 27 simultaneously read the patient examination information from the RFID tags of the blood-sampling tubes in the prepared tray (FIG. 7 (d)).

Since the reading device 27 is arranged near the first lifting means 25 in this embodiment, while moving the prepared tray up and down by the first lifting means 25, it is possible to simultaneous reading of the patient examination information from the RFID tags of the articles (the blood-sampling tubes and the hand pasting label if needed) stored in the tray by the reading device 27. As above mentioned, in case that the reading device 27 may read the patient examination information from the RFID tags of the articles stored in the tray while moving the prepared tray so as to move the articles in the tray, it is also possible to skip the process of returning the prepared tray to the read position L4 again.

As shown in FIGS. 7(b) and 7(c), since the prepared tray is inclined once by the first lifting means 25, the blood-sampling tubes move within the tray so as to change the state/orientation of the RFID tags provided in the labels pasted on the blood-sampling tubes within the prepared tray. Thereby, the state/orientation of the RFID tags stored in the prepared tray are changed by moving the prepared tray and then the reading device 27 may simultaneously read the patient examination information of the RFID tags again. As a result, the reading error which may arise according to the state/orientation of the articles in the tray may be reduced.

The number of times of performing this retry control may be decided arbitrarily.

In case that even if the retry control is performed predetermined number of times, the patient examination information read from the RFID tags do not coincide with the instruction information of the doctor, the control means 31 stops the retry control and performs an error process.

As long as the error process may inform a user that the patient examination information read from the RFID tags do not coincide with the instruction information of the doctor, arbitrary processes may be used for the error process.

For example the error process may be a process which suspends the automatic blood-sampling tube preparation system, and emits an alarm and/or a warning lamp, etc.

According to the above mentioned automatic blood-sampling tube preparation system, when the patient examination information read from the RFID tags do not coincide with the instruction information of the doctor, the retry control is performed. In the retry control, the state/orientation of articles such as the blood-sampling tubes in the tray are changed, and then the control means has a function that makes the reading device read the patient examination information from the RFID tags again. Therefore, there may be reduced the reading error which may arise according to the state/orientation of articles, such as the blood-sampling tubes in the tray. Therefore, when exact numbers of articles are stored in the tray, control device 31 does not judge that the patient examination information read from the RFID tags do not coincide with the instruction information of the doctor owing to the reading error by the reading device. Therefore, the control means 31 does not stop the operation of the automatic blood-sampling tube preparation system owing to the reading error by the reading device. Therefore, according to the automatic blood-sampling tube preparation system concerning this embodiment, it becomes possible to perform exact and efficient processing.

Since the above-mentioned automatic blood-sampling tube preparation system changes the state/orientation of the blood-sampling tubes in the prepared tray by controlling the first lifting means that takes out the empty tray and the conveyor belts which transport the prepared tray, it does not need to add the mechanism for exclusive use only for the retry control. Therefore, in order to perform the retry control, a complicated composition is not needed, and the retry control can apply to the existing automatic blood-sampling tube preparation system easily.

Furthermore, since the reading device 27, the first lifting means 25 and the second lifting means 26 are arranged between the two conveyor belts 24 for transferring the tray in the automatic blood-sampling tube preparation system, the whole system is compact.

Also, in the above-mentioned automatic blood-sampling tube preparation system, the blood-sampling tube receiving position L1, the read position L4, the empty tray receiving position L2 and the prepared tray discharge position L3 are arranged in a straight line in order. Therefore, in the read position L4 between the blood-sampling tube receiving position L1 and the prepared tray discharge position L3, the reading process by the reading device 27 and the retry control process can be performed while transferring the prepared tray to the prepared tray discharge position L3 from the blood-sampling tube receiving position L1.

In the above-mentioned embodiment, the states/orientations of the articles such us the blood-sampling tube or the like in the tray are changed by inclining the prepared tray using the first lifting means 25 so that the state/orientation of the RFID tags is changed. However, without limiting this composition to this embodiment, the automatic blood-sampling preparation system may be constituted such that the control device has a function that makes the conveyor belts 24 rapidly move forward so as to change the states/orientations of the articles contained in the tray on the conveyor belts. Also the mechanism for exclusive using to only change the states/orientations of the articles in the tray may be provided on the automatic blood-sampling preparation system.

In the above-mentioned embodiment, the states of the articles such us the blood-sampling tube or the like in the tray are changed by inclining the prepared tray using the first lifting means 25 so that the state of the RFID tags is changed. However, without limiting this composition to this embodiment, the automatic blood-sampling preparation system may be constituted such that the control device has a function that makes the conveyor belts 24 rapidly move forward so as to change the states of the articles contained in the tray on the conveyor belts. Also the mechanism for exclusive using to only change the states of the articles in the tray may be provided on the automatic blood-sampling preparation system.

When performing the retry control two or more times, the container transferring means may be controlled to combine different operations such that the prepared tray is inclined by means of the first lifting means in the 1st retry control and then the prepared tray is moved by making the conveyor belts 24 rapidly move forward and rapidly stop in the 2nd retry control.

Furthermore, in the above-mentioned embodiment, the control device is constituted such that the retry control may be performed if the patient examination information read from the RFID tags do not coincide with the patient examination information included in the instruction information of the doctor. The comparison of the patient examination information read from the RFID tags and the doctor's instruction information may also include the comparison of the number of the articles with RFID tag contained in the prepared tray and the number of the blood-sampling tubes included in the instruction information. Therefore the control device may be constituted to recognize the number of the articles (the blood-sampling tubes and the hand pasting labels if needed) contained in the prepared tray on the basis of the patient examination information read from the RFID tags by the reading device and to perform the retry control if the recognized number of the articles do not coincide with the number of the blood-sampling tubes included in the instruction information.

Furthermore the control device may be constituted such that when the patient examination information read from the RFID tags and the patient examination information included in the instruction information of the doctor are compared one by one so that the patient examination information included in the instruction information remains, the control device judges the they do not coincide, and performs the retry control.

In the above mentioned embodiment, the automatic blood-sampling tube preparation system comprises the automatic blood-sampling tube preparation device and the blood-sampling tube recovery device. Said preparation device includes a plurality of the blood-sampling tube containing sections put on multi stage, in which the blood-sampling tubes are laid down horizontally. And said recovery device collects the label pasted blood-sampling tubes discharged from the preparation device in the tray.

However the construction of the automatic blood-sampling tube preparation system according to the present invention is not limited to this embodiment. For example, the preparation system according to the present invention may comprise one device which takes out one or more required blood-sampling tubes from the blood-sampling tube containing sections, makes the identification RFID tag labels, pastes the each label on the each blood-sampling tube, and collects the label pasted tubes into the suitable container for each patient.

Also the automatic blood-sampling tube preparation system according to the present invention may be constituted as follows. For example, the blood-sampling tube containing section may comprise a rack in which one or more blood-sampling tubes are held in a standing condition. And the transferring means may comprise a robot arm which operates with the X-Y axis established on said rack. In this case, the control device may be constituted to make the prepared rack transferring conveyor rapidly move forward and rapidly stop so as to change the states/orientations of the blood-sampling tube contained in the rack.

Furthermore, in the above embodiment, the label processing means is constituted to print the patient examination information corresponding to the blood-sampling tube transferred by the blood-sampling tube transferring means on the label and write the information on the RFID tag. However, the construction of the label processing means is not limited to this embodiment. For example the label processing means may be constituted only to write the patient examination information on the RFID tag without performing printing on the label.

Also, in the above mentioned embodiment, the label processing means is constituted to write the patient examination information on the RFID tags of the label. However, the construction of the label processing means is not limited to this embodiment. For example, the processing means may be constituted to directly write the patient examination information on the RFID tag previously incorporated in the blood-sampling tube.

What is claimed is:

1. An automatic blood-sampling tube preparation system comprising:

at least two blood-sampling tube containing sections, each section being intended to contain blood-sampling tubes of a same type, a tube transferring device positioned to selectively remove a blood-sampling tube required for use in the examination of a blood sample of a patient by a doctor from one of the blood-sampling tube containing sections and transfer the removed blood-sampling tube, a writing device positioned to receive blood-sampling tubes from the tube transferring device and write patient examination information onto an RFID tag disposed on the blood-sampling tubes, a discharge conveyor positioned to receive said blood-sampling tubes from the writing device and discharge said blood-sampling tubes to a container positioned on a blood-sampling tube recovery device, the blood-sampling tube recovery device including the container which is configured to receive the blood-sampling tubes per each patient and travel along a transferring path of the blood-sampling tube recovery device, a reading device which is arranged along the transferring path of the blood-sampling tube recovery device which is constituted to read simultaneously all patient examination information from all the RFID tags of the blood-sampling tubes contained in the container in which the blood-sampling tubes have been received per each patient while the container is transferred by the blood-sampling tube recovery device, a control device which is constituted to receive instruction information by a doctor in which the patient examination information for each patient is included, control the operation of the tube transferring device, the writing device, the blood-sampling tube recovery device and the reading device, and compare the patient examination information read from the RFID tags by the reading device with the instruction information to determine whether the patient examination information matches the instruction information, characterized in that the control device is programmed to control the operation of the blood-sampling tube recovery device to make the container move so as to change or alter the state/orientation of the tubes and therefor the RFID tags attached to those tubes contained in the container in response to the control device determining that the patient examination information read from the RFID tags does not match the instruction information, and then the control device controls the reading device to read the patient examination information from the RFID tags contained in the container again, and then the control device compares the patient examination information and the instruction information; and wherein said automatic blood sampling tube recovery device includes either a lifting device to lift said container and/or at least one conveyor for transferring said container;

whereby the control device controls the lifting device such that only a part of the container is lifted by the lifting device so as to change or alter the state/orientation of the tubes and therefor the RFID tags attached to those tubes contained in the container; and/or whereby the control device controls the conveyor such that the conveyor rapidly starts to move in a first direction and then either moves in a second direction and/or rapidly stops so as to change or alter the state/orientation of the tubes and therefor the RFID tags attached to those tubes contained in the container.

2. The automatic blood-sampling tube preparation system according to claim 1, wherein the automatic blood-sampling tube preparation system further comprises an instruction paper issuing device which is constituted to make a pasting label with a RFID tag onto which the patient examination information is written and then discharges the pasting label with the RFID tag to the container, said container contains the blood-sampling tubes with the RFID tag onto which the patient examination information has been written as well as the pasting label with the RFID tag to which the patient examination information has been written, said reading device reads simultaneously all patient examination information from the blood-sampling tube and the pasting label with the RFID tag, and said control device compares the patient examination information read from the blood-sampling tube and the pasting label with the RFID tag with the instruction information.

3. The automatic blood-sampling tube preparation system according to claim 1, wherein the automatic blood-sampling tube preparation system further comprises a pasting roller which is constituted to automatically paste the RFID tag on the blood-sampling tube transferred by said tube transferring device and said writing device is constituted to write the patient examination information onto the RFID tag.

4. The automatic blood-sampling tube preparation system according to claim 3, wherein the automatic blood-sampling tube preparation system further comprises a printer which is constituted to print the patient examination information on a surface of the RFID tag.

5. The automatic blood-sampling tube preparation system according to claim 1, wherein the automatic blood-sampling tube preparation system further comprises an instruction paper issuing device which is constituted to make a pasting label with a RFID tag onto which the patient examination information is written and then discharges the pasting label with the RFID tag to the container.

6. The automatic blood-sampling tube preparation system according to claim 2, wherein the automatic blood-sampling tube preparation system further comprises a pasting roller that is constituted to automatically paste the RFID tag on the blood-sampling tube transferred by said tube transferring device and said writing device is constituted to write the patient examination information onto the RFID tag.

7. The automatic blood-sampling tube preparation system according to claim 2, wherein the automatic blood-sampling tube preparation system further comprises a printer that is constituted to print the patient examination information on a surface of the RFID tag.

8. The automatic blood-sampling tube preparation system according to claim 2, wherein said instruction paper issuing device is constituted to write the patient examination information onto the pasting label with the RFID.

* * * * *